(12) United States Patent
Pecor

(10) Patent No.: US 6,494,903 B2
(45) Date of Patent: Dec. 17, 2002

(54) OVER THE WIRE HEAT EXCHANGE CATHETER WITH DISTAL VALVE

(75) Inventor: Robert Pecor, Viejo, CA (US)

(73) Assignee: Alsius Corporation, Irvine, CA (US)

( * ) Notice: Subject to any disclaimer, the term of this patent is extended or adjusted under 35 U.S.C. 154(b) by 24 days.

(21) Appl. No.: 09/851,654

(22) Filed: May 8, 2001

(65) Prior Publication Data

US 2001/0032003 A1 Oct. 18, 2001

Related U.S. Application Data

(63) Continuation of application No. 09/366,640, filed on Aug. 2, 1999, now Pat. No. 6,287,326.

(51) Int. Cl.[7] .................................................. A61F 7/00
(52) U.S. Cl. ........................ 607/105; 607/104; 606/21
(58) Field of Search ........................ 607/96, 104, 105; 606/20, 21, 22, 23, 27, 28

(56) References Cited

U.S. PATENT DOCUMENTS 5,957,963 A * 9/1999 Dobak, III .................... 606/20
6,165,196 A * 12/2000 Stack et al. .................. 606/194

* cited by examiner

Primary Examiner—Roy D. Gibson
(74) Attorney, Agent, or Firm—Burns, Doane, Swecker & Mathis, L.L.P.

(57) ABSTRACT

An over-the-wire heat exchange catheter includes a heat transfer extension having at least one supply lumen and at least one return lumen for circulating heat exchange fluid within the catheter. The catheter has a distal tip and valve attached to the distal tip. The valve automatically seals the distal tip around a guidewire or a mandrel to seal the heat transfer extension and inhibit escape of the heat transfer fluid from the heat transfer extension.

12 Claims, 9 Drawing Sheets

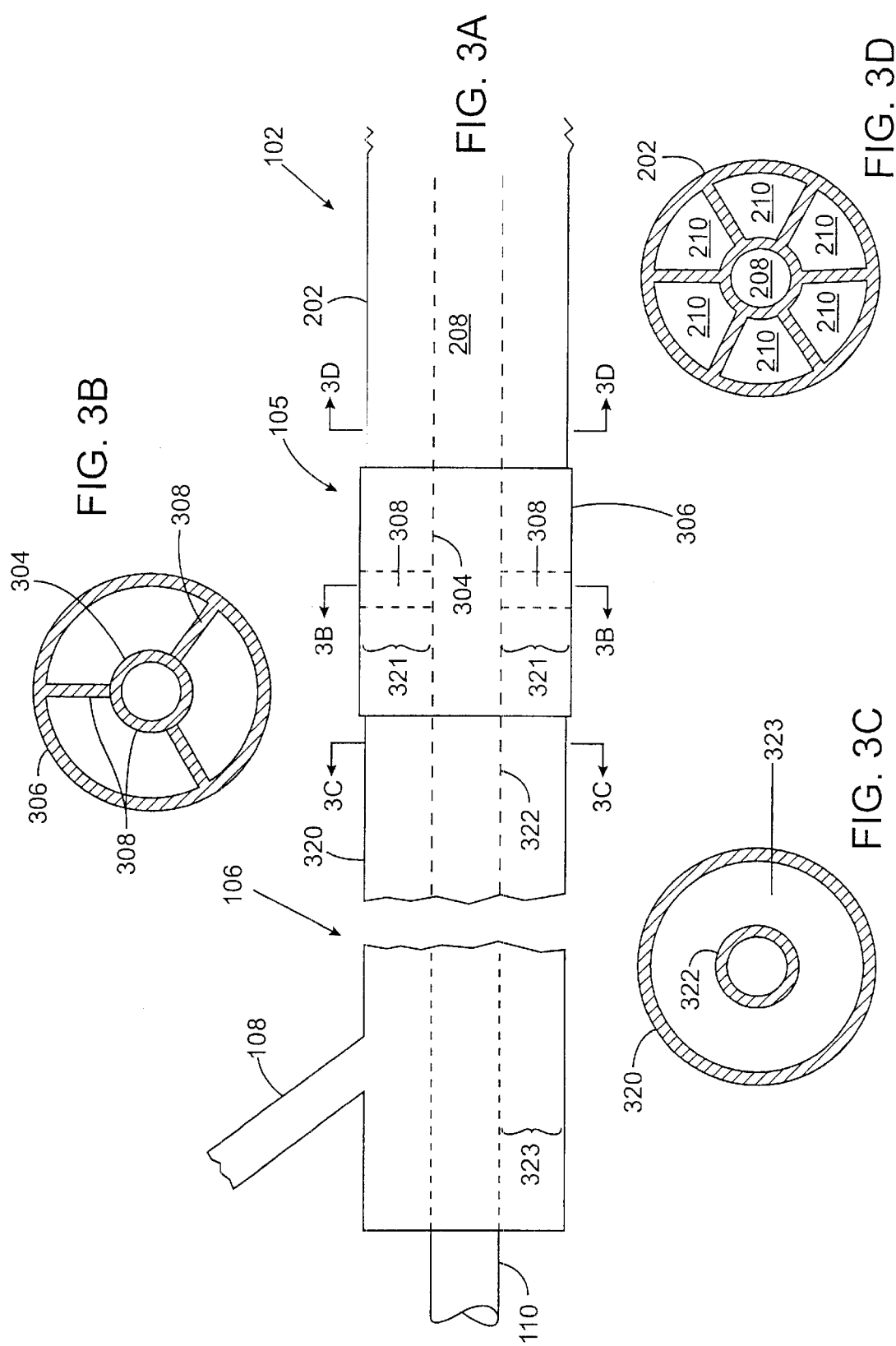

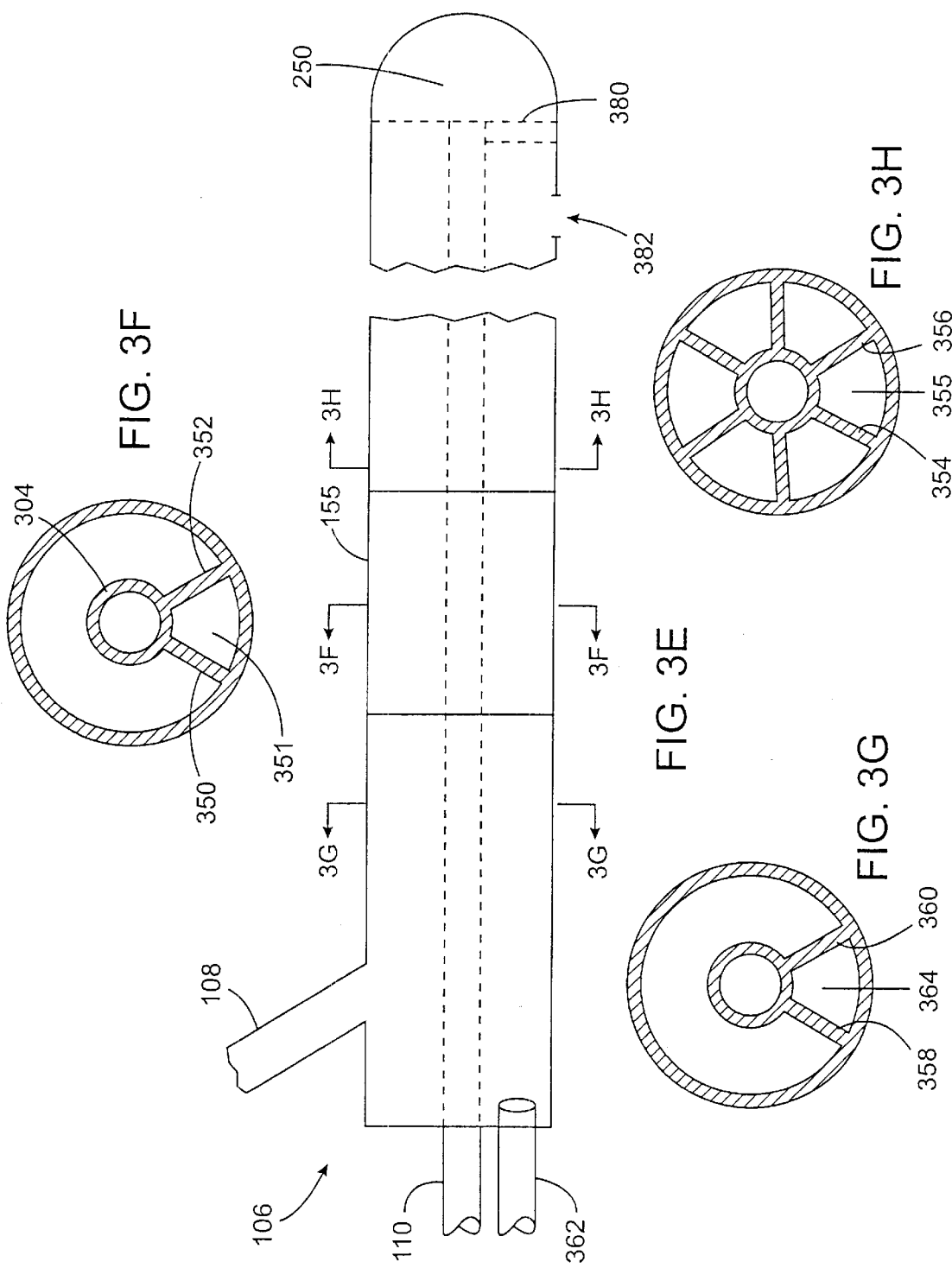

OVER THE WIRE HEAT EXCHANGE CATHETER WITH DISTAL VALVE

CROSS-REFERENCE TO RELATED APPLICATION

This is a Continuation of U.S. patent application Ser. No. 09/366,640, filed Aug. 2, 1999 now U.S. Pat. No. 6,287,326, the disclosure thereof is incorporated herein by reference.

FIELD OF THE INVENTION

The present invention relates to over the wire heat exchange catheters, particularly to catheters having a distal end with a coiled heat exchanger.

BACKGROUND

In warm blooded creatures, temperature regulation is one of the most important functions of the body. Despite the known importance of properly maintaining body temperature, scientists have discovered certain beneficial effects of artificially inducing a hypothermic state. For instance, cooling the body can help regulate vital functions during surgery by lowering the metabolism. With stroke, trauma, and other conditions, hypothermia is believed to reduce the permeability of the blood/brain barrier. Also, induced hypothermia is believed to inhibit the release of damaging neurotransmitters, inhibit calcium mediated effects, inhibit brain edema, and lower intra cranial pressure. Regardless of the particular mechanism, the present invention understands that fevers degrade the outcomes for patients suffering from brain trauma or stroke, and moreover that hypothermia improves the outcomes for such patients.

Hypothermia may be induced locally or systemically. With local hypothermia, physicians focus their cooling efforts on a particular organ, limb, anatomical system, or other region of the body. With systemic hypothermia, body temperature is lowered without particular attention to any body part.

One technique for inducing systemic hypothermia includes packing the patient's entire body in ice. Although this technique has been used with some success, some physicians may find it cumbersome, and particularly time consuming. Also, it is difficult to precisely control body temperature with ice packing. As a result, the patient's body temperature overshoots and undershoots the optimal temperature, requiring physicians to add or remove ice. Furthermore, there is some danger of injuring the skin, which is necessarily cooled more than any other body part.

In another approach to systemic hypothermia, the patient is covered with a cooling blanket, such as an inflatable air-filled or water-filled cushion. Physicians control the patient's temperature by regulating the temperature of the inflation medium. Nonetheless, some delay is still inherent, first for a cooling element to change the temperature of the cooling medium, and then for the temperature adjusted cooling medium to cool the desired body part. This delay is even longer if the targeted body part is an internal organ, since the most effective cooling is only applied to the skin, and takes some time to successively cool deeper and deeper layers within the body.

A proven approach to inducing hypothermia is by circulating a cooling fluid through a cooling catheter placed inside a patient's body. The catheter may be inserted into veins, arteries, cavities, or other internal regions of the body. It is often desired to precisely position such a catheter within the body of a patient to provide for local, or, systematic heat exchange.

SUMMARY

An over-the-wire heat exchange catheter includes a heat transfer extension having at least one supply lumen and at least one return lumen for circulating heat exchange fluid within the catheter. The catheter has a distal tip and valve attached to the distal tip. The valve automatically seals the distal tip around a guidewire or a mandrel to seal the heat transfer extension and inhibit escape of the heat transfer fluid from the heat transfer extension.

The valve is normally closed, but opens upon receipt of a guide wire and seals the distal tip around the guidewire. The valve automatically closes upon removal of the guide wire to re-seal the distal tip to inhibit escape of the heat exchange fluid from the heat transfer extension.

The valve has a disk shape and an aperture for admitting a guidewire. The aperture is a centrally defined aperture for admitting a guidewire, and opposing concave sides. According to aspects of the invention, the valve is made from silicon or plastic. According to another aspect of the invention, the valve includes sealed flaps. According to a further aspect of the invention, the valve includes a spongy membrane.

The heat transfer extension includes a flow through lumen to deliver fluids via the distal tip of the catheter.

BRIEF DESCRIPTION OF THE DRAWING FIGURES

FIG. 3A is a plan view of the catheter of FIG. 1 illustrating fluid flow paths of the invention in greater detail.

FIGS. 3B, 3C and 3D are different cross-sectional diagrams of the catheter of FIG. 3A, according to the invention.

FIG. 3E is a plan view of the catheter of FIG. 3A illustrating an alternative embodiment capable of exchanging fluid with the patient, in accordance with the invention.

FIGS. 3F, 3G and 3H are different cross-sectional diagrams of the catheter of FIG. 3E, according to the invention.

DETAILED DESCRIPTION OF THE INVENTION

The nature, objectives, and advantages of the invention will become more apparent to those skilled in the art after considering the following detailed description in connection with the accompanying drawings.

The invention concerns a catheter with a sealed multi-lumen heat transfer extension designed to internally circulate a coolant, and thereby cool tissue or fluid surrounding the catheter. The elongated heat transfer extension contains multiple lumens longitudinally spanning the heat transfer extension. In an exemplary embodiment, these lumens include a central lumen surrounded by multiple peripheral lumens. In this embodiment, the central lumen constitutes a supply lumen, whereas the peripheral lumens constitute return lumens (or vice-versa). A distal fluid exchange reservoir provides a fluid redirecting path between the central lumen and the peripheral lumens.

The catheter has largely coextensive coolant supply and return lines, connected at a distal end to the coiled multi-turn heat transfer extension. The heat transfer extension is coupled to the supply/return lines by a fluid transfer housing. The fluid transfer housing forms a sealed fluid path between the return lumen and the return line, and also forms a sealed fluid path between the supply lumens and the supply line.

A cooling fluid ("coolant") travels longitudinally out and back through a sealed path inside the catheter, without contacting the tissue or body fluid surrounding the catheter. This catheter directs coolant down the supply line and supply lumens to the catheter's tip, where the coolant reverses direction in the fluid exchange reservoir. Returning fluid progresses from the fluid exchange reservoir through the return lumen, and then the return line.

The coolant comprises a fluid having suitable properties of heat transfer, biocompatibility, viscosity, etc. The coolant may be a liquid or gas, with saline being one example. As an alternative to coolant, a suitable heating fluid may be used to induce hyperthermia rather that hypothermia.

Figure 1:
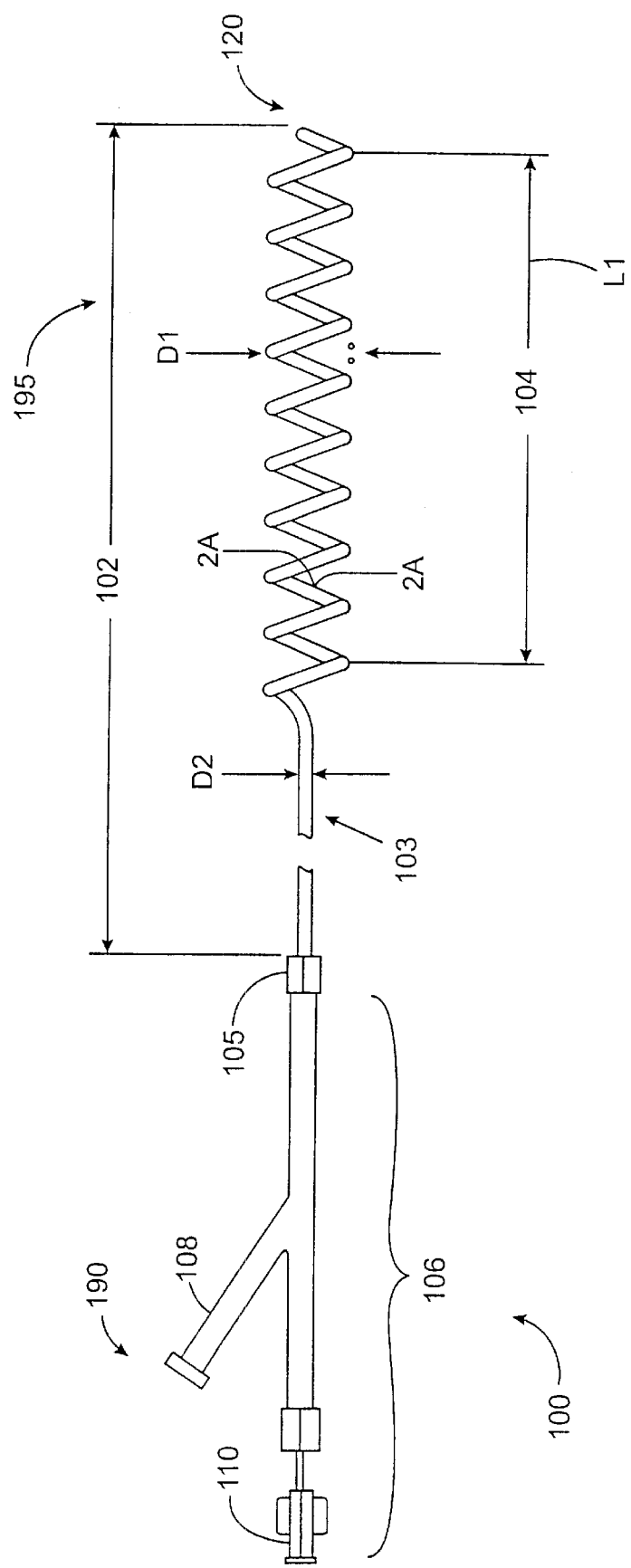
FIG. 1 is a plan view of the hardware components and interconnections of a catheter with a coiled, multi-lumen heat transfer extension, in accordance with the invention.

FIG. 1 shows a catheter 100 that exemplifies this invention. The catheter 100 includes an elongated coiled multi-turn heat transfer extension 102, a fluid transfer housing 105, and a pump interface 106. For ease of explanation, the catheter 100 and its subcomponents are discussed in terms of a proximal end 190 (or direction) and a distal end 195 (or direction).

The heat transfer extension 102 is a sealed construct that internally circulates a coolant, and thereby cools adjacent bodily tissue or fluid surrounding the catheter. The heat transfer extension 102 comprises a suitably flexible and nonallergenic material with consistent mechanical performance over a range of expected temperatures such as 0–40° Celsius. Some exemplary materials include poly ether amide block copolymers, polyurethane, polyethylene, poly vinyl chloride, and the like. The heat transfer extension 102 comprises a tube-shaped member that includes a coiled region 104 and a straight region 103. At a distal tip 120, the extension 102 includes a distal fluid reservoir (described below, which may be referred to as a "plenum." This fluid reservoir provides a fluid redirecting path between the supply lumens and the return lumen.

For use in the inferior vena cava, the extension 102 may have an overall length of about 100 centimeters when straight (about 50 centimeters when coiled. The coiled region 104 has a length "$L_1$" of about 15 centimeters when configured into repeating coils, where each coil has a diameter "$D_1$" of about two centimeters. When pulled straight, the coiled region 104 would have a length of about 65 centimeters. The tube-shaped member that constitutes the heat transfer extension 102 may have a diameter "$D_1$" of about 0.04 centimeters. Ordinarily skilled artisans (having the benefit of this application) should understand that the different relative lengths of coiled and straight regions 104,103 may be used, with one possibility even being elimination of any straight region whatsoever.

The extension 102 is coupled to the pump interface 106 by the fluid transfer housing 105. Alternatively, the fluid transfer housing 105 may be omitted from the invention, with the heat transfer extension 102 being coupled directly to the interface 106. The pump interface 106 provides a means for supplying coolant to the extension 102 and receiving a return flow of coolant therefrom. As an example, the pump interface 106 may comprise a "Y" connector, as described in the parent application identified above. The interface 106 includes a coolant supply connector 108 and a coolant return connector 110, each coupled to respective lines (not shown) running internally along the length of the interface 106. The connector 110 may comprise a well known Luer port, for example.

Internally, the extension 102 includes one or more supply lumens, and one or more return lumens. Cooperatively, the supply/return lumens carry fluid out to the extension's distal tip and back. The housing 105 couples the return lumens) to the lines leading to the coolant return connector 110, and the supply lumens) to the lines leading to the coolant supply connector 108.

Figure 2A:
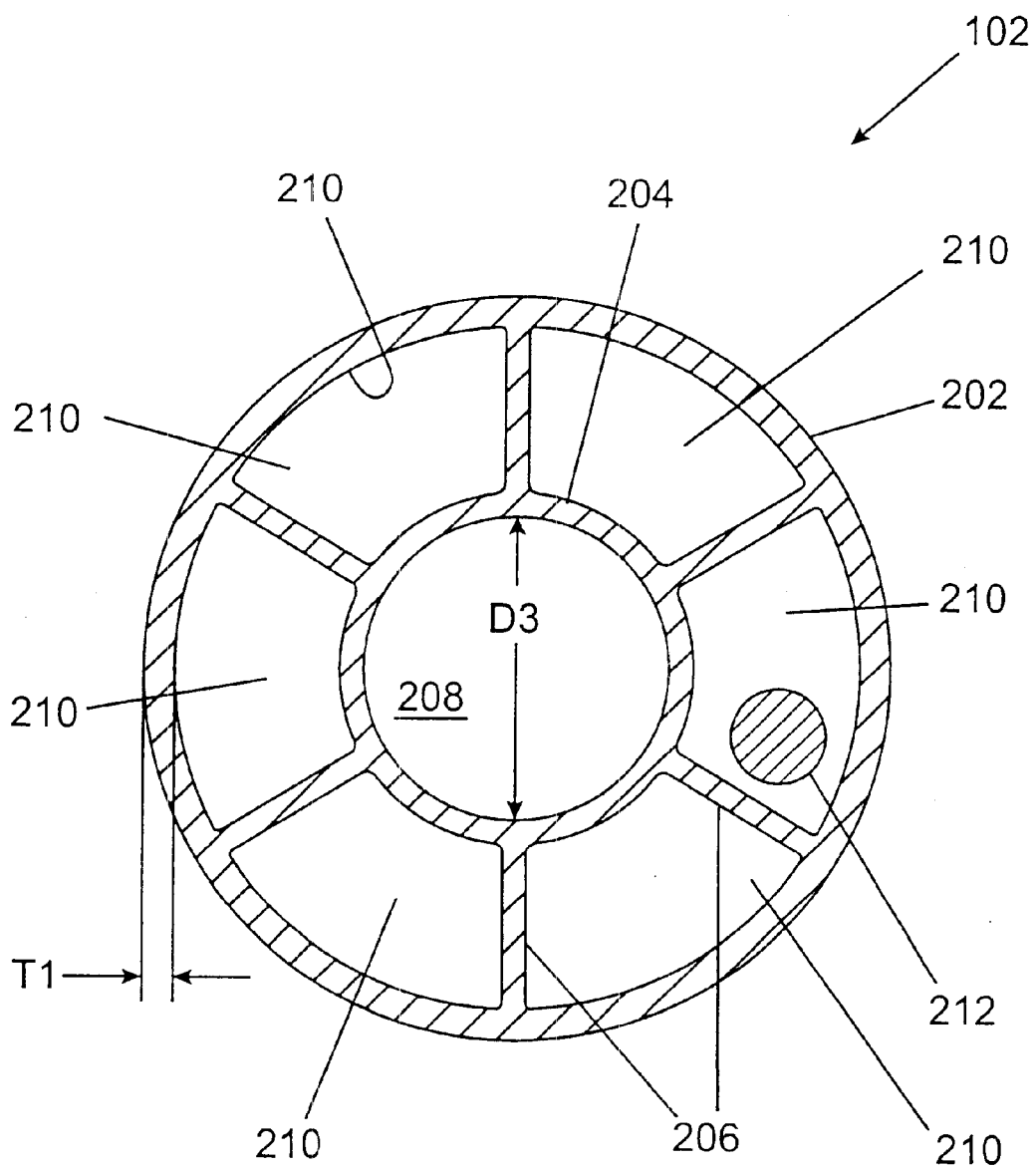
FIG. 2A is a cross-sectional view of the heat transfer extension of the catheter of FIG. 1 taken across the line 2A—2A, in accordance with the invention.

FIG. 2A shows one exemplary construction of the heat transfer extension 102. In this example, the extension 102 includes a single return lumen 208 central to the tube, and several supply lumens peripherally located around the return lumen. The extension 102 includes an outer wall 202 and a concentric inner wall 204. A number of ribs 206 hold the walls 202, 204 a fixed distance apart, and prevent the outer wall 202 from collapsing. The inner wall 204 defines a central longitudinal lumen 208, and the walls 202, 204 and ribs 206 cooperatively define multiple longitudinal peripheral lumens 210. The peripheral lumens 210 are also referred to as "supply" lumens, because they are used to carry coolant outward to the catheter's distal tip; in contrast, the central lumen 208 may be referred to as a "return lumen" because it carries coolant returning to the interface 106 from the heat transfer extension's distal tip. Relatedly, the housing 105 couples the return lumen to the coolant return connector 110, and the supply lumens to the coolant supply connector 108, as discussed in more detail below.

The invention contemplates various structure for providing heat transfer extension 102 with its coiled shape. In one embodiment, the heat transfer extension 102 is permanently coiled by heat treating or another process. In another embodiment, represented in FIG. 2A, the heat transfer extension 102 additionally includes a shaping wire 212 that runs longitudinally along the length of the tube 102 within one of the peripheral lumens 210. The shaping wire 212 comprises a shape memory substance causing the wire to assume a coiled shape under certain "shape-active" temperatures and a non-coiled shape under other "shape-relaxed" temperatures. The introduction of shape memory into the shaping wire 212 is discussed in greater detail below, along with other manufacturing operations. As a specific example, the wire may comprise a material such as nickel-titanium (e.g., Nitinol) with a diameter of about 0.05 millimeters. In a different embodiment, the shaping wire 212 may be omitted, with shape memory being introduced directly (i.e., built-in to) into the heat transfer extension material itself. For this purpose, shape memory polymeric materials such as specialized polyurethane may be used. As a further embodiment, the shaping wire 212 may be used along with some built-in shape memory incorporated into the tube material, albeit a lesser amount than necessary without the shaping wire 212.

Preferably, the dimensions of the lumens are chosen to balance fluid flow resistance in the return lumen 208 against collective fluid flow in the supply lumens 210, thereby minimizing the overall resistance of fluid traversing the extension 102. In the illustrated example, there are six ribs 206. According to one exemplary implementation, the extension 102 may have an overall diameter ("$D_2$", FIG. 1) of about 0.4 centimeters, with the walls 202, 204 and the ribs 206 each having a thickness ("$T_1$," FIG. 2A) of about 0.18 millimeters. In this example, the central lumen 208 has an inner diameter ("$D_3$," FIG. 2A) of about 1.6 millimeters.

Figure 2B:
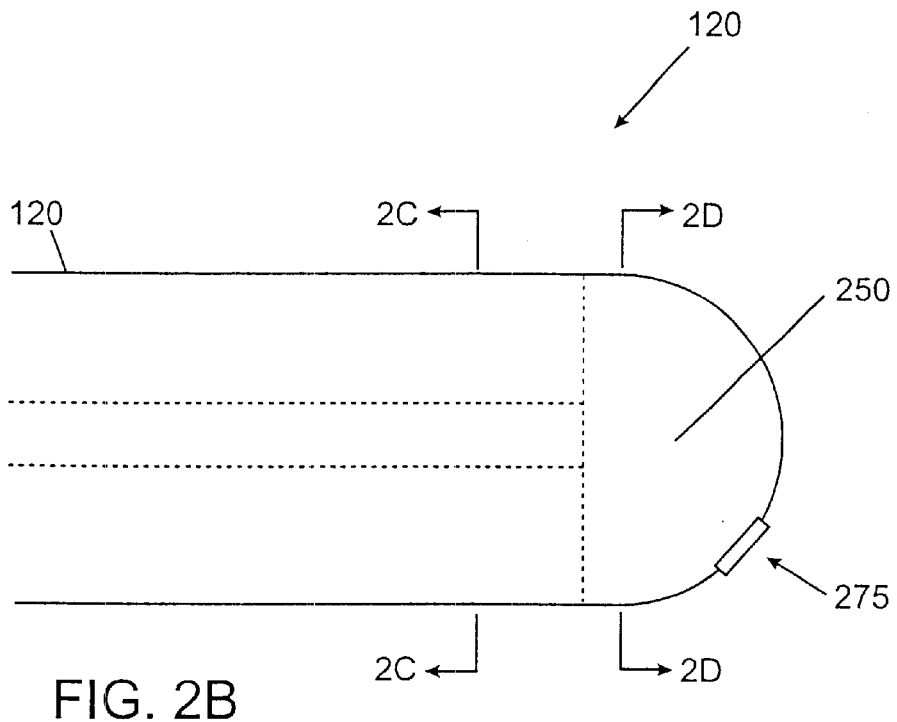
FIG. 2B is a plan view of the catheter of FIG. 1 showing the distal tip in greater detail, with portions shown in phantom, according to the invention.

FIG. 2B shows the distal tip 120 of the extension 102 including a "distal fluid reservoir 250, also referred to as a "plenum." The fluid reservoir 250 includes a region where fluid from the various lumens mixes and re-circulates.

Figure 2C:
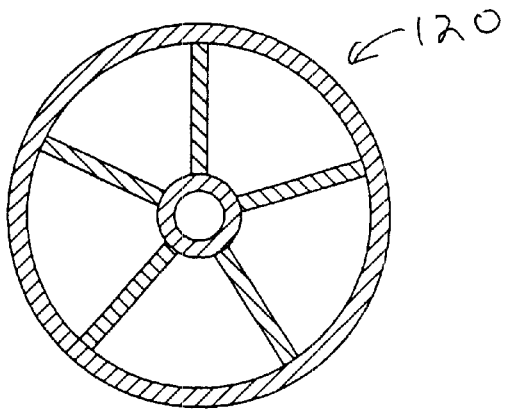
FIG. 2C is a cross-sectional view of the catheter of FIG. 2B as seen along the line 2C—2C.
Figure 2D:
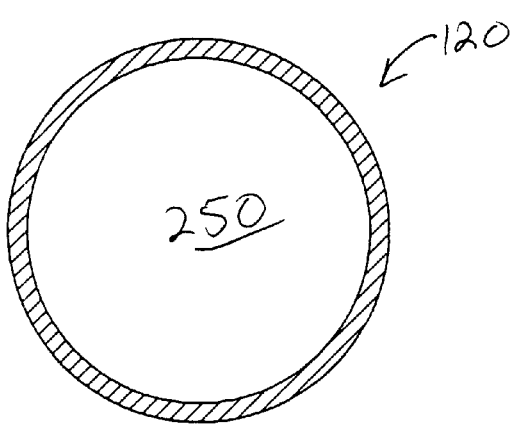
FIG. 2D is a cross-sectional view of the catheter of FIG. 2B as seen along the line 2D—2D.

FIG. 2C shows the distal tip 120 defining lumens proximally of the reservoir 250 of FIG. 2B. FIG. 2D shows the distal tip 120 defining the fluid reservoir 250.

FIG. 2B shows the distal tip 120 including a valve 275 defined on the distal tip 120. The catheter in accordance with the present invention may be used in "over the wire" applications, where a straight, rigid guide wire (not shown) is inserted into the body, and then the catheter is slid over the wire into place. For "over the wire" use, the catheter's distal tip includes the valve 275 to selectively admit a guide wire or "mandrel" in the direction toward the proximal end of the extension 102.

The valve 275 also re-seals itself when the guide wire is removed in the opposite direction.

Figure 2F:
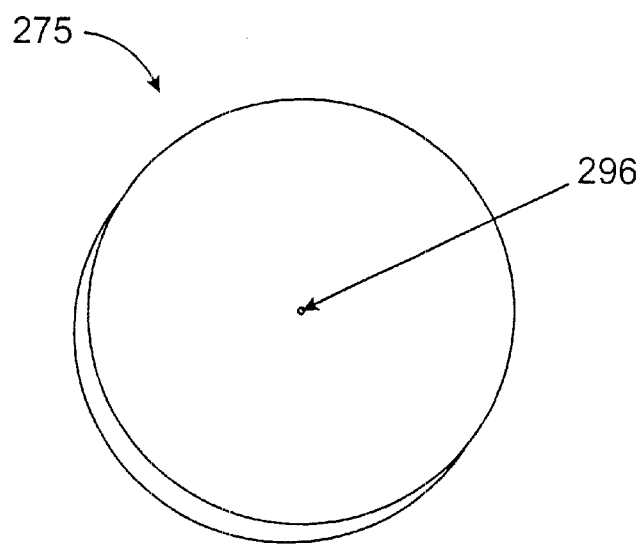
FIG. 2F is a perspective view of the valve of FIG. 2E, according to the invention.
Figure 2E:
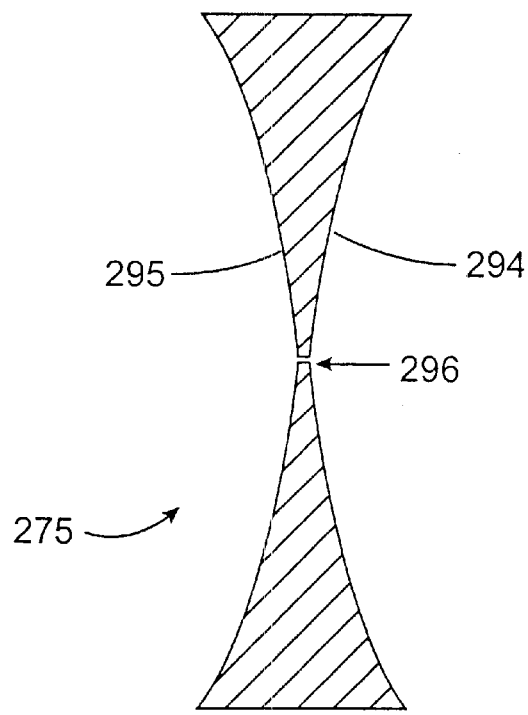
FIG. 2E is a cross-sectional diagram of a valve for use in "over the wire" applications according to the invention.

FIGS. 2E and 2F shows the valve 275 having a disk shape. The valve 275 has opposing concave sides 294 and 295. The valve has a central aperture 296 sized to normally seal upon itself and, alternatively, to admit and seal upon a guidewire. As the guide wire (not shown) passes through the aperture 296, it temporarily enlarges the aperture 296. However, due to the softness and elasticity of the valve 275, the valve 275 returns to its original state when the guide wire is removed. Accordingly, the valve 275 is made from material of suitable elasticity, hardness, biocompatibility, and other properties to suit these purposes. Some exemplary materials include silicon or plastics.

According to various aspects of the invention, the valve 275 includes an aperture with one or more normally seated (and sealed flaps, a spongy membrane, a mechanical device, or another suitably penetrable but resealable member. In "over the wire" applications the catheter is positioned in a patient's body by sliding the catheter over the guide wire, such that the guide wire passes into one of the lumens.

FIG. 3A shows various components of the heat transfer extension 102 connected to the pump interface 106. FIG. 3A also diagrams the fluid flow paths between heat transfer extension lumens, the fluid transfer housing 105, and the pump interface 106. Generally, the fluid transfer housing 105 couples the extension 102 to the pump interface 106, and includes an outer casing 306 and a transfer pipe 304. At one end, the casing 306 is sealed to the outer wall 202 of the extension 102. At the opposite end, the casing 306 is sealed to an outer wall 320 of the pump interface 106.

FIG. 3B shows the pipe 304 held in place by various ribs 308. Three ribs 308 extend from the pipe 304 at 120° angles. The ribs 308 keep the pipe 304 in a sufficiently central position to align it with the central lumen 208. The ribs 304 extend the full length of the housing 105 (from end to end) according to one aspect of the invention.

At one end, the pipe 304 is sealed to the central lumen 208, which is shown in FIG. 3D. At the opposite end, the pipe 304 is sealed to a return line 322 of the pump interface 106, shown in FIGS. 3A and 3C. The return line 322 of the pump interface 106 ultimately connects to the return connector 110.

The housing 105 facilitates fluid flow between the central lumen 208 and the return connector 110 using the pipe 304. In the opposite direction, a passageway 321 (FIG. 3A) between the casing 306 and the pipe 304 permits fluid flow between the coolant supply connector 108 and the supply lumens 210. Namely, fluid flows from the supply connector 108 into a passageway 323 between the return line 322 and the outer wall 320 (FIGS. 3A, 3C), then into the passageway 321 between the casing 306 and pipe 304, and finally into the supply lumens 210 (FIG. 3D). The passageway 323 between the return line 322 and outer wall 320 may be referred to as a "supply line."

FIGS. 3E, 3F, 3G and 3H illustrate an embodiment, where one lumen is specially configured to deliver or receive fluid to/from the patient during while the catheter is deployed. This lumen may be referred to as a flow-through lumen. In FIG. 3E, the flow-through lumen is provided by dedicating one of the (peripherally located) supply lumens, as shown by 355 (FIG. 3H).

The flow-through lumen 355 meets a barrier 380 (FIG. 3E) that prevents fluid from the lumen 355 from mixing in the reservoir 250. The flow-through lumen 355 is provided with an opening 382 (FIG. 3E) enabling fluid to flow into and/or out of the distal end of the lumen 355. At the flow-through lumen's proximal end, the fluid transfer housing 155 includes ribs 350 and 352 (FIG. 3F) that define a flow-through passageway 351 that seals to the flow-through lumen 355. The fluid transfer housing 105 in this embodiment may omit the ribs 308 of FIG. 3A, since the pipe 304 is now held in place by the ribs 350, 352 required to define the flow-through passageway 351.

As shown in FIG. 3G, the sealed flow path defined by the flow-through lumen 355 and passageway 351 continues inside the pump interface 106 by virtue of ribs 358, 360 located therein, these ribs defining a flow-through passageway 364. The passageway 364 vents to a flow-through port 362 (FIG. 3E).

The flow-through lumen 355 may be employed the purpose of delivering materials (such as medicine) to the patient, sampling materials (such as blood) from the patient, etc. For example, to deliver medicine to the patient, the medicine is first-introduced into the port 362. The medicine flows through the passageway 364, the passageway 351, the flow-through lumen 355, and finally exits the heat transfer extension 102 through the opening 382 into the patient's blood, other fluid/tissue that immerses the catheter.

Although not illustrated, more than one of the lumens may be configured as flow-through lumens, being sure to leave at least one supply and one return lumen to form a continuous coolant flow path. In this way, various concurrent operations can be performed, such as concurrently sampling and delivery, delivering different medicines simultaneously, etc.

To further enhance the operation of the catheter 100, several additional features may be provided. First, the catheter 100 may be manufactured with one or more radiopaque markers, to assist physicians in positioning the catheter 100 with x-rays. As one option, distal and proximal regions may be separately marked to easily identify the outer dimensions of the heat transfer extension 102. To further enhance the catheter's radioactive signature, the entire catheter 102 may incorporate a radiopaque material of contrasting intensity with the distal/proximal markers. An example of one radiopaque substance is Barium Sulfate. As another feature, a coating of heparin or another anticlotting agent may be applied to outer portions of the tube 102 or any other regions with exposure to a patient's blood. This helps discourage clotting of blood surrounding the catheter 100 during use.

Figure 4:
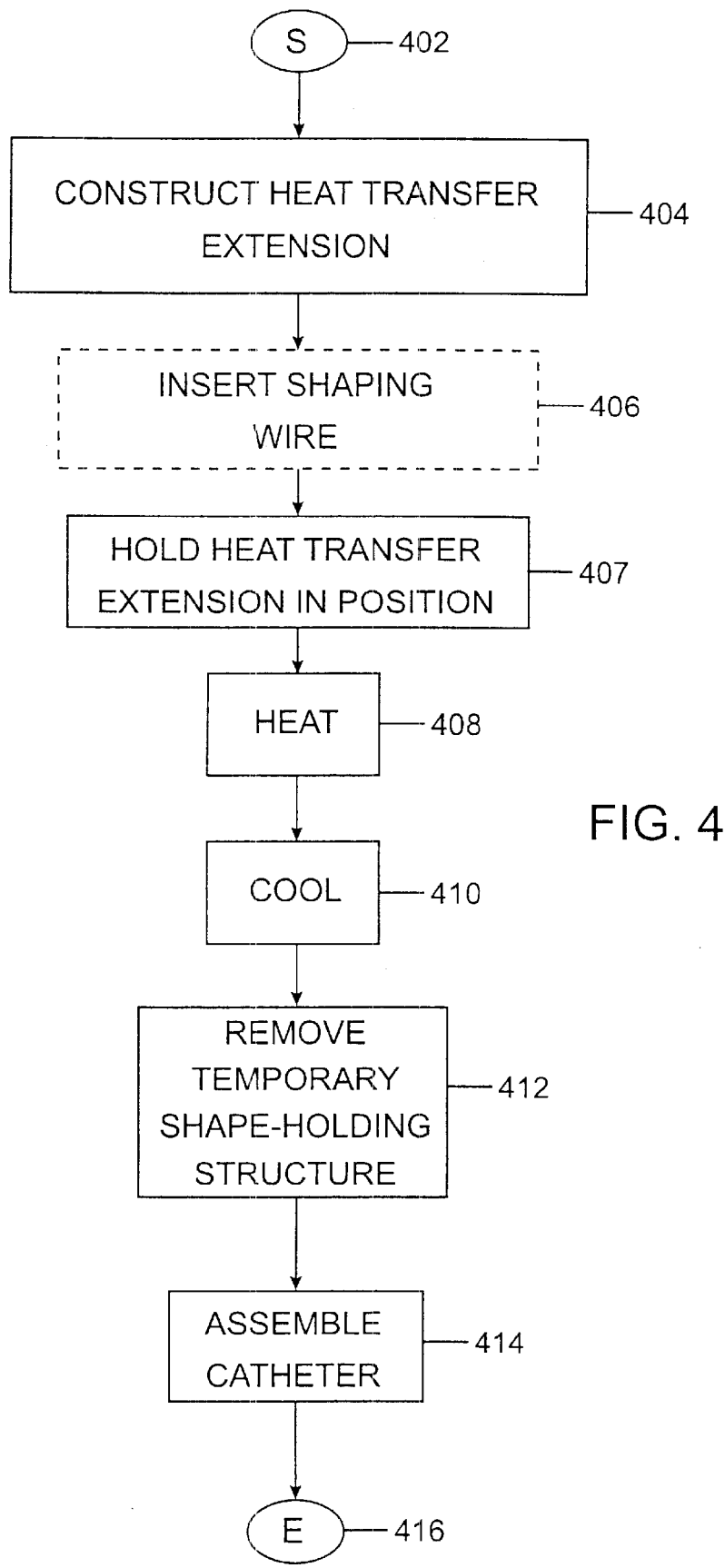
FIG. 4 is a flowchart of an operational sequence for manufacturing the catheter of FIG. 1 in accordance with the invention.

FIG. 4 shows a sequence 400 of exemplary operations for constructing one example of the various embodiments of catheter of this invention. For ease of explanation, but without any intended limitation, the example of FIG. 4 is described in the specific context of the catheter 100 (FIG. 1) described above. Step 402 marks the beginning of the sequence 400. In step 404, technicians construct the heat transfer extension 102. The extension 102, including the tube, walls, and lumens as discussed above may be constructed using extrusion, vacuum molding, or another suitable technique.

After step 404, technicians insert the shaping wire 212 into one of the peripheral lumens 210 (step 406). This step may be omitted, however, by constructing the heat transfer extension out of materials having their own shape memory properties, or by using a permanently shaped structure. Whether the shaping wire 212 is used or not, technicians act in step 407 to position the heat transfer extension into the desired coiled shape. The heat transfer extension may be held in such form by means of a metal forming wire, scaffolding, or other positioning structure.

After step 406, the heat transfer extension is placed into an oven (step 408) and heated. Heating is conducted in order to introduce shape memory into the shaping wire 212 and/or the heat transfer extension itself, or to permanently shape the heat transfer extension, depending upon the properties of the materials used.

Figure 5:
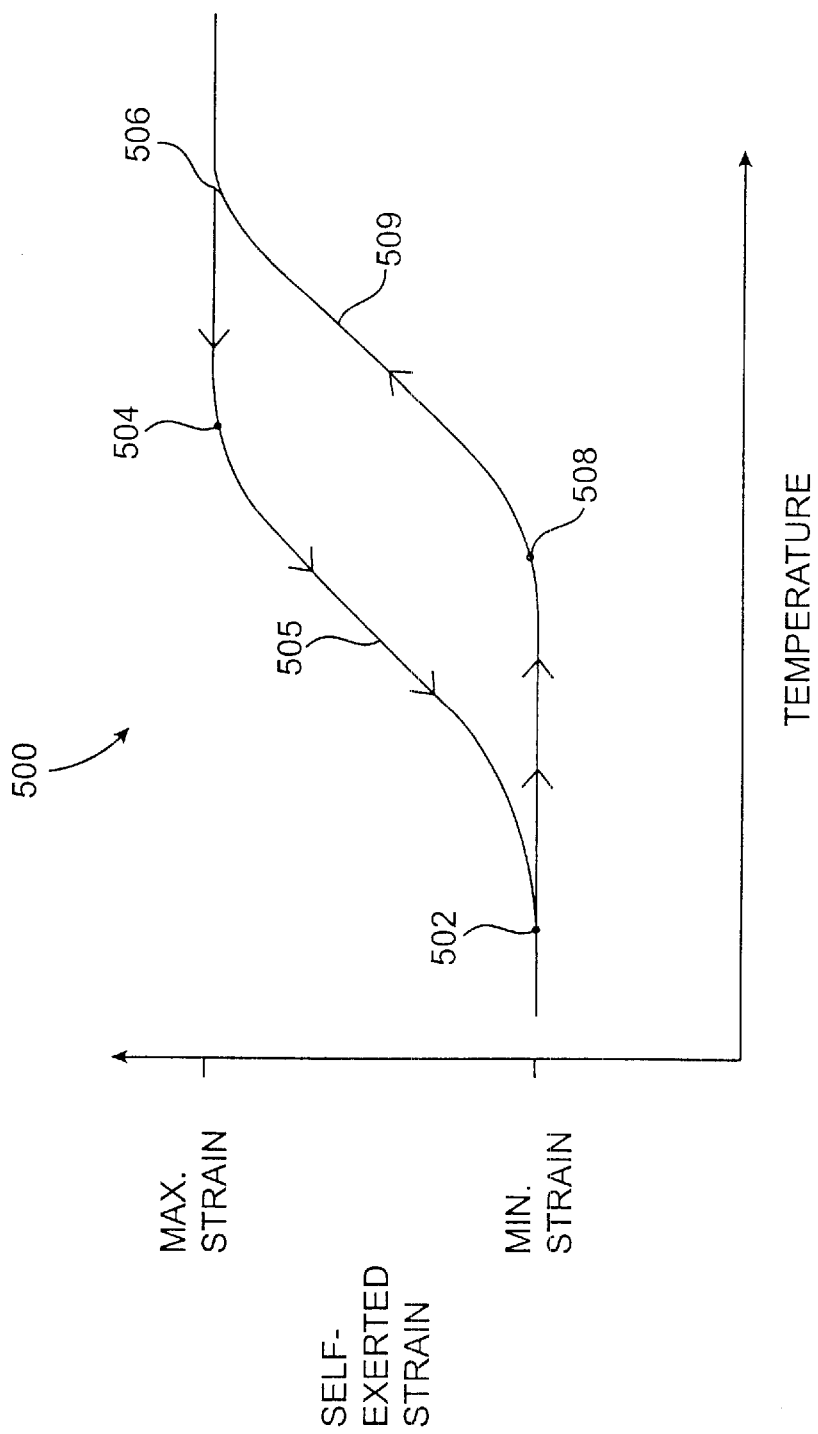
FIG. 5 is a diagram showing the self exerted strain properties of shape memory material over a range of temperatures.

In the case of shape memory materials (e.g., shaping wire 212 or heat transfer extension substance, the heating of step 408 is conducted according to FIG. 5. Referring to FIG. 5, the heat transfer extension's initial temperature is indicated at 502, or less. At this point, the extension has little or no self-exerted strain. As more heat is applied, the extension reaches a temperature indicated at 508. At this temperature 508, shape memory begins to be instilled in the heat transfer extension's shape memory structure (i.e., the wire or the built-in shape memory materials). With greater temperatures, a greater level of self-exerted strain is introduced into the extension, as shown by the temperature/strain path indicated at 509. Finally, upon arriving at a desired temperature 506, the oven is operated to hold a steady temperature. This temperature 506 may, for example, be the temperature providing maximum self-exerted strain. This temperature varies according to the material.

After maintaining the temperature indicated at 506 for a sufficient time, such as one hour, the heat transfer extension is cooled. One exemplary cooling technique involves immersing the extension in cold water. The extension is immersed until it cools sufficiently for the materials to adopt, as a default shape, the coiled shape held during heating.

During cooling, the temperature of the heat transfer extension subsides along a path 505, ultimately returning (and optionally passing) the initial temperature 502. Upon reaching the temperature 502, the shape-memory-equipped heat transfer extension once again has minimal self-exerted strain.

After the heat transfer extension has been heated and cooled in steps 408, 410 to introduce shape memory, temperatures at and beneath the point 502 are considered "shape-relaxed," since they induce minimal self-exerted strain in the heat transfer extension. In contrast, temperatures above this point are "shape-active," since they cause the heat transfer extension to assume the form held during original oven heating. Past the temperature 502, even greater temperatures induce proportionally greater self-exerted strain in the heat transfer extension.

As an alternative to steps 408, 410, where materials of the heat transfer extension are susceptible to permanent shaping rather than shape memory, step 408 heats the material beyond a fixing temperature, then step 410 cools the material to permanently retain its coiled shape. As a further alternative, steps 408, 410 may introduce a combination of strong or weak permanent shaping (e.g., the tube material itself) as desired, along with temperature-dependent shaping (e.g., the shaping wire 212).

After step 410, technicians in step 412 remove the metal forming wire or other temporary forming structure used to hold the shape of the extension 102 (as installed by step 407). Then, the newly shaped heat transfer extension is assimilated with the other components of the catheter 100, such as the pump interface 106, fluid transfer housing 105, and the like (step 414). After step 414, the sequence 400 ends in step 416.

Figure 6:
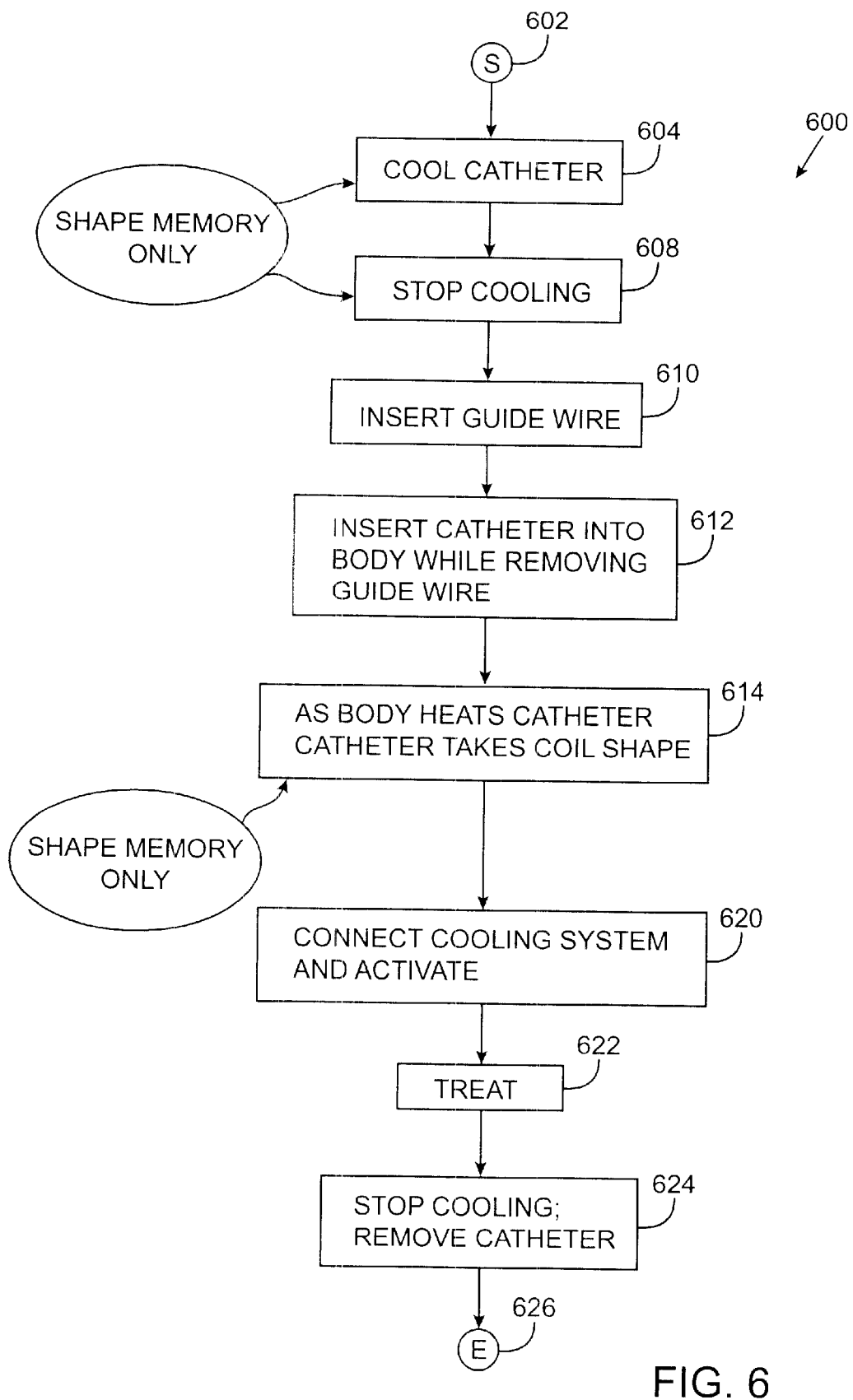
FIG. 6 is a flowchart of an operational sequence for using the catheter of FIG. 1 with a patient, in accordance with the invention.

FIG. 6 illustrates a sequence of exemplary operations 600 for utilizing a catheter of this invention to treat a patient. For ease of explanation, but without any intended limitation, the example of FIG. 6 is described in the specific context of the catheter 100 (FIG. 1) described above. Prior to the steps 600, physicians prepare the patient (not shown) for treatment. This may involve cleaning and disinfecting skin, removing hair, administering medicine, and other known procedures to ready the patient for surgery or other treatment. Also prior to the steps 600, physicians prepare an existing body opening or create a new opening for insertion of the catheter 100. As an example of creating a new opening, doctors may cut an appropriately located incision or puncture for insertion of the catheter into the interior vena cava, using the Seldinger technique.

Step 602 marks the beginning of the sequence 600. Steps 604, 608 are only performed for catheters with a shape-memory-equipped heat transfer extension, e.g., shaping wire 212 or built-in shape memory. In step 604, the shape-memory catheter 100 is cooled to its shape-relaxed temperature range. Namely, while the catheter 100 is outside the body, physicians attach the pump interface 106 to a coolant source and circulate coolant to/from the catheter 100. The coolant source may comprise, for example, a syringe, mechanized pump, hand pump, gravity feed system, or another appropriate device for circulating a coolant fluid through the catheter 100. Coolant is supplied at the coolant supply connector 108, and flows down the pump interface 106. Due to positive pressure upon coolant arriving from the supply connector 108, the coolant passes from the passageway 323 of the pump interface 106 through the fluid transfer housing 105, where it is routed into the supply lumens of the extension 102. The coolant then travels through the supply lumens to the distal reservoir 250. The distal reservoir 250 redirects supply fluid into opposite direction travel down the return lumen. Then, the housing 105 directs fluid from the return lumen into the return line 322 inside the interface 106, and ultimately to the coolant return port 110. Of course, the opposite direction fluid path may be used instead, without departing from the scope of this invention. When the catheter 100 is cooled sufficiently, physicians stop the cooling of step 608.

After steps 604, 608 are performed (shape memory embodiments only), physicians insert a guide wire (not shown) into the catheter 100 (step 610). For this operation, the pump interface 106 is removed from the catheter 100, leaving the catheter's proximal end open. Insertion of the guide wire has the effect of initially straightening the coils of a permanently shaped heat transfer extension, or further straightening the coils of a shape-memory-equipped heat transfer extension (which are already somewhat straight due to the shape relaxed state induced by the cooling of step 604).

With the guide wire in place, the operation of inserting the catheter into the patient begins (step 612). The distal tip of the catheter 100 is slid into the opening in the patient's body. If desired, the catheter may be inserted through an introducer sheath (not shown), nozzle, tube, funnel, or another device designed to ease catheter insertion. The catheter 100 and guide wire are slidably moved into the patient's body. During this process, the guide wire protrudes out of the proximal end of the housing 105. Next, while moving the catheter 100 further into the patient's body, physicians begin to simultaneously remove the guide wire in proportion to the inward movement of the catheter.

Insertion of the catheter and removal of the guide wire continues until the guide wire is completely removed, and the catheter resides at its desired position. This completes step 612. As an alternative to the foregoing embodiment of step 612, the catheter may be inserted "over the wire." The "over the wire" catheter includes a distal valve 275 to selectively admit the guide wire into one of the lumens, and automatically re-seal itself when the wire is removed. In this embodiment, step 612 is performed by inserting the guide wire into the body first, and then sliding the catheter's distal end upon the guide wire's proximal end. The guide wire's proximal end proceeds into the catheter via the pass-through valve 275. With guidance from the "over the wire" guide wire, the catheter is slidably moved into the desired position in the patient's body, and the guide wire is withdrawn.

After completion of step 612, whether "over the wire" or not, removal of the guide wire permits a permanently shaped heat transfer extension coil into its normal shape right away. In the case of shape memory induced coils, step 614 assists the catheter in reaching its coiled state. Namely, as body heat warms the heat transfer extension, the shape memory material experiences increasing self-induced strain, tending to coil the extension. Next, physicians couple the catheter to the coolant circulating system as discussed above, and begin to circulate the coolant through the catheter (step 620). Coolant circulates through the catheter. As it circulates, the coolant removes body heat because of the supply lumens' thin walls and their substantial surface area that is exposed to the surrounding liquid (e.g., arterial or venous blood, etc.) that immerses the catheter 100. Coolant may be circulated, for example, at the rate of 400 milliliters per minute. Physicians commence surgery or other treatment of the patient (step 622) when the targeted body region reaches a desired temperature. Arrival at this temperature may be recognized by measuring the temperature of a concentrated target region (localized hypothermia), or measuring the body core temperature (systemic hypothermia).

In addition to cooling, the catheter may be used for other purposes during treatment. As mentioned above, certain of the lumens may be configured as flow through lumens for the purpose of exchanging materials with the patient. With this hardware embodiment, treatment of step 622 may also be accompanied by using these lumens for delivering materials such as medicine to the patient, and/or sampling substances such as blood from the patient.

After the treatment of step 622 is complete, physicians stop circulating the coolant and remove the catheter in step 624. Or, depending upon the treatment being performed, physicians may decide to continue operating the catheter for some time after treatment ends. For example, the patient can be re-warmed in a controlled manner after therapeutic hypothermia by using the body core temperature as a feedback signal to cause less-cool or possibly warm (>38° Celsius) saline to flow through the catheter. In re-warming the patient, the system monitors the rate of warm-up rate to avoid re-warming too rapidly or too slowly.

The catheter is removed by re-inserting the guide wire while simultaneously withdrawing the catheter. Insertion of the guide wire is useful to straighten the coils, and thereby configure the catheter for easy removal. As another part of step 624, the patient's incision (if any) is closed and any other applicable post treatment procedures are performed. The sequence ends in step 626.

The treatment technique 600 provides a number of distinct advantages. For example, the heat transfer extension provides a substantial amount of heat exchange because its coiled configuration (in the body) provides a large surface area within a compact volume. As another benefit, the technique 600 helps minimize blood clotting because of the catheter's design. Namely, the catheter of this invention provides a continuous smooth surface from end to end, thereby avoiding angular junctions, narrow passages, binding components, and other structures that might tend to form blood clots.

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated.

Moreover, the present invention is presently described in the context of the human body merely for ease of illustration, without any intended limitation. The invention may also be employed to help mammals, birds, reptiles, or other creatures. Furthermore, although the foregoing discussion has described catheter use to induce a hypothermic state, ordinarily skilled artisans (having the benefit of this disclosure) will recognize that the invention also contemplates the use of catheters to induce systemic or local hyperthermia. Additionally, although certain fluid flow paths have been specifically illustrated for ease of understanding, opposite direction flow paths may be used instead. In such alternatives, references to "supply" or "return" lines or ends are accordingly reversed.

What is claimed is:

1. A catheter, comprising:
   a distal tip having a valve for admitting a guidewire and for sealing upon removal of the guidewire;
   an elongate heat transfer extension housing at least one supply lumen and at least one return lumen running longitudinally along the extension, the extension also including a distal fluid exchange reservoir providing a fluid redirecting path between the supply and return lumens; and
   shape memory structure causing the heat transfer extension to assume a coiled shape under predetermined shape-active temperatures and a non-coiled shape under predetermined shape-relaxed temperatures different from the shape-active temperatures.

2. A heat exchange catheter as set forth in claim 1, wherein the valve means opens upon receipt of a guide wire to seal the distal tip around the guidewire, the valve automatically closes upon removal of the guide wire to re-seal the distal tip and inhibit escape of the heat exchange fluid from the heat transfer extension.

3. A heat exchange catheter as set forth in claim 1, wherein the valve means has a disk shape and an aperture for admitting a guidewire.

4. A heat exchange catheter as set forth in claim 1, wherein the valve means is made from silicon.

5. A heat exchange catheter as set forth in claim 1, wherein the valve means includes a spongy membrane.

6. A heat exchange catheter as set forth in claim 1, wherein the valve means is elastic.

7. The catheter of claim 1, wherein the valve is positioned at the distal tip of the extension, the valve opening upon receipt of a guide wire into the extension via the valve, and the valve substantially closing upon removal of the guide wire from the valve.

8. A catheter, comprising an elongate heat transfer extension housing, a guidewire valve with a disk shape and a central aperture, at least one supply lumen and at least one return lumen running longitudinally along the extension, the extension also including a distal fluid exchange reservoir providing a fluid redirecting path between the supply and return lumens, where at least a portion of the heat transfer extension has a coiled shape with multiple coil turns.

9. A heat exchange catheter, comprising:
   an elongate heat transfer extension housing at least one supply lumen and at least one return lumen, the extension including a distal fluid exchange reservoir providing a fluid redirecting path between the supply and return lumens,
   a distal tip attached to the heat transfer extension, the distal tip having a seal means for selectively admitting a guidewire; and
   a shape memory means for causing the heat transfer extension to assume a coiled shape under predetermined shape-active temperatures and a non-coiled shape under predetermined shape-relaxed temperatures, the shape-active temperatures having a shape-active temperature range the shape-relaxed temperatures having a shape-relaxed temperature range that differs from the shape-active temperature range.

10. The catheter of claim 9, wherein the seal means defines an aperture that normally closes upon itself, admittance of a guidewire through the aperture opens the aperture and causes the seal means to seal around the guidewire, and the seal means closes the aperture upon removal of the guide wire to seal the distal tip.

11. The catheter of claim 10, wherein the seal means comprises:
   a disk-shaped member having a periphery attached to the distal tip, the disk-shaped member having at least one concave side, the aperture being defined centrally within the disk-shaped member.

12. The catheter of claim 10, wherein the seal means comprises:
   a disk-shaped member having a periphery attached to the distal tip, the disk-shaped member having opposing concave sides, the aperture being defined centrally within the disk-shaped member.

* * * * *